United States Patent [19]
Barnett

[11] Patent Number: 5,967,982
[45] Date of Patent: Oct. 19, 1999

[54] NON-INVASIVE SPINE AND BONE REGISTRATION FOR FRAMELESS STEREOTAXY

[75] Inventor: Gene H. Barnett, Gates Mills, Ohio

[73] Assignee: The Cleveland Clinic Foundation, Cleveland, Ohio

[21] Appl. No.: 08/987,406

[22] Filed: Dec. 9, 1997

[51] Int. Cl.$^6$ ........................................... A61B 6/00
[52] U.S. Cl. ........................... 600/429; 606/130; 378/206; 600/426
[58] Field of Search ..................... 600/429, 407, 600/414, 417, 473, 476, 425–427; 606/130; 378/205, 206, 37, 163, 164, 166

[56] References Cited

U.S. PATENT DOCUMENTS

| | | |
|---|---|---|
| 3,577,160 | 5/1971 | White . |
| 4,365,341 | 12/1982 | Lam . |
| 4,793,355 | 12/1988 | Crum et al. . |
| 4,896,673 | 1/1990 | Rose et al. . |
| 4,930,506 | 6/1990 | Brisson . |
| 5,013,317 | 5/1991 | Cole et al. . |
| 5,070,861 | 12/1991 | Einars et al. . |
| 5,099,846 | 3/1992 | Hardy . |
| 5,189,690 | 2/1993 | Samuel . |
| 5,224,147 | 6/1993 | Collin et al. . |
| 5,230,338 | 7/1993 | Allen et al. . |
| 5,260,985 | 11/1993 | Mosby . |
| 5,309,913 | 5/1994 | Kormos et al. . |
| 5,517,990 | 5/1996 | Kalfas et al. . |
| 5,588,430 | 12/1996 | Bova et al. . |
| 5,595,177 | 1/1997 | Mena et al. . |
| 5,622,170 | 4/1997 | Schulz . |
| 5,662,111 | 9/1997 | Cosman . |
| 5,682,890 | 11/1997 | Kormos et al. . |
| 5,732,703 | 3/1998 | Kalfas et al. . |
| 5,772,594 | 6/1998 | Barrick . |
| 5,776,064 | 7/1998 | Kalfas et al. . |

OTHER PUBLICATIONS

J. Neurosurg./vol. 74/May 1991—article entitled "A frameless, armless navigational system for computer–assisted neurosurgery".

Patrick Clarysse et al./vol. 10, No. 4, Dec. 1991—article entitled "A Computer–Assisted System for 3–D Frameless Localization in Stereotaxic MRI".

S. James Zinreich, MD et al./Radiology 1993; vol. 188, pp. 735–742 entitled "Frameless Stereotaxic Integration of CT Imaging Data: Accuracy and Initial Applications".

*Primary Examiner*—Jeffrey R. Jastrzab
*Assistant Examiner*—Shawna J Shaw
*Attorney, Agent, or Firm*—Fay, Sharpe, Beall, Fagan, Minnich & McKee, LLP

[57] ABSTRACT

An interventionalist or operator uses a variety of apparatus 30 including tools, tool guides, and pointers in a procedure on a region of interest. The region of interest was previously the subject of a diagnostic imaging procedure to generate three dimensional diagnostic image data, selective slices or other portions of which are displayable on video monitors 34. The position of the apparatus 30 in operator space is determined by actuating emitters 32, receiving the emitted signals with receivers 12, and calculating the position of the pointer in operator space. A pair of radio translucent constructions 14, 16 each carry a plurality of radiopaque markers 18 which are positioned adjacent the region of interest. Two or more projection images are taken through the region of interest and the radiopaque markers using a movable x-ray tube 22 and radiation detector 24. The operator uses a control 36 to position cursors on corresponding anatomical markers in both the projection images and images from the diagnostic data to determine a correlation or transform between projection image space and diagnostic data space. The operator positions a tip of the pointer 30 on each of the radiopaque markers and actuates the emitters 32 to determine the position of the radiopaque markers in operator space, i.e. to correlate operator space with projection image space. In this manner, the correlation or transform between operator space and diagnostic data space is generated through the intermediary of projection image space.

16 Claims, 4 Drawing Sheets

NON-INVASIVE SPINE AND BONE REGISTRATION FOR FRAMELESS STEREOTAXY

BACKGROUND OF THE INVENTION

The present invention relates to the medical diagnostic and surgical arts. It finds particular application in conjunction with stereotactic surgery and will be described with particular reference thereto. It will be appreciated, however, that the invention will also find application in conjunction with minimally invasive surgery, neurosurgery, neurobiopsy, CT-table needle body biopsy, breast biopsy, endoscopic procedures, orthopedic surgery, other invasive medical procedures, industrial quality control procedures, and the like.

Three-dimensional diagnostic image data of the brain, spinal cord, and other body portions is produced by CT scanners, magnetic resonance imagers, and other medical diagnostic equipment. These imaging modalities typically provide structural detail with a resolution of a millimeter or better.

Various frameless stereotactic procedures have been developed which take advantage of the three-dimensional image data of the patient. These procedures include guided-needle biopsies, shunt placements, craniotomies for lesion or tumor resection, and the like. Another area of frameless stereotaxy procedure which requires extreme accuracy is spinal surgery, including screw fixation, fracture decompression, and spinal tumor removal.

In one prior art technique, the fiducials or other markers which are imaged substantially as points in the diagnostic imaging process are affixed to the patient's head or other stable region of interest before the image data is generated. In this manner, the fiducials appear as points in the resultant image data. Before the frameless stereotaxy procedure, a pointer is touched to each of the fiducials and actuated to generate a position indicating signal. By touching the pointer to several fiducials and actuating it, a plurality of points corresponding to the fiducials are determined in the coordinate system of the pointer, operator space. The coordinates of the fiducials are readily identified in the coordinate system of the diagnostic data. As illustrated in U.S. Pat. No. 5,309,913, once a plurality of corresponding coordinates are known in two different coordinate systems, the mathematical transform for transforming coordinates of one coordinate system into the other is readily calculated.

For some medical procedures, the use of fiducials is inconvenient or inappropriate. For example, in spine surgery, the spine is separated from the outer surface of the skin by muscle and fat tissue. Accordingly, fiducials affixed to the skin during an imaging procedure are apt to shift relative to the spine, when the patient moves. However, the spine itself has many small, distinctive structures, such as points that are readily identified in the diagnostic image. Once the surgery is started and the spine is exposed, the pointer is positioned on these distinctive structures and actuated to mark the structures in the pointer coordinate system. The corresponding points in the diagnostic image are identified and their coordinates determined. In this manner, natural, anatomical fiducials are used instead of artificial fiducials. They are again imaged in a fixed relationship to the region of interest during the imaging procedure.

However, there are other regions of the anatomy, such as the organs, to which fiducials cannot be attached conveniently and which lack pointer accessible, accurate anatomical fiducials or marker points.

The present invention provides a new and improved apparatus and method which overcomes the above-referenced problems and others.

SUMMARY OF THE INVENTION

A registration apparatus for a diagnostic imaging system determines a position of a tip of a wand relative to an anatomy of a subject in a patient space relative to a position of the wand tip and the anatomy in three-dimensional diagnostic image data. The apparatus includes at least three emitters for emitting signals indicative of the position of the wand, at least two receivers for receiving the signals, a first image memory for storing the three-dimensional diagnostic image data indicative of the anatomy of the subject, a selecting means for selecting data from the first image memory, and a display for converting the selected data from the first image memory into human-readable displays. First and second reference plates are positioned at a first location and a second location, respectively. The first and second locations are known and on opposing sides relative to the subject. Each reference plate includes at least three non-collinear radiopaque marks at known locations. An x-ray source is positioned at one of a third location and a fourth location. The third and fourth locations are known relative to the first and second locations. An x-ray detector is positioned at one of a fifth location and a sixth location. The fifth and sixth locations are known relative to the first and second locations. X-rays are projected from the x-ray source, through the reference plates and the subject and onto the x-ray detector to generate projection images of the three radiopaque marks and the anatomy of the subject. The x-ray detector is positioned at the fifth location when the x-ray source is positioned at the third location. The x-ray detector is positioned at the sixth location when the x-ray source is positioned at the fourth location. A correlator correlates the position of the wand tip relative to the anatomy in the patient space with the position of the anatomy in the three-dimensional diagnostic image data.

In accordance with another aspect of the present invention, a method of correlating positions of a tool or tool guide in operator space with coordinates of diagnostic data and image space is provided. A first projection image is projected through a region of interest of a subject in a first direction and a second projection image is generated in a second direction. Corresponding anatomical markers in the first and second projection images and in the diagnostic image data are identified. From the corresponding anatomical markers in the three images, the projection images are correlated with the diagnostic image data to correlate projection image space with diagnostic data space. Projection image space is then coordinated with operator space within which a tool or tool guide is positioned. In a procedure, coordinates of the tool or tool guide are determined in operator space. Through the correlation between operator space and projection image space and the correlation between projection image space and diagnostic data space, the position of the tool or tool guide in operator space is correlated with a corresponding position in diagnostic data space.

One advantage of the present invention is that it does not require gaining access to the optimal characteristic points of the patient's spine or other anatomy.

Another advantage of the present invention is that it enables particularly characteristic structures which are not readily accessible to be used for a more accurate registration between the patient and electronic diagnostic image data.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
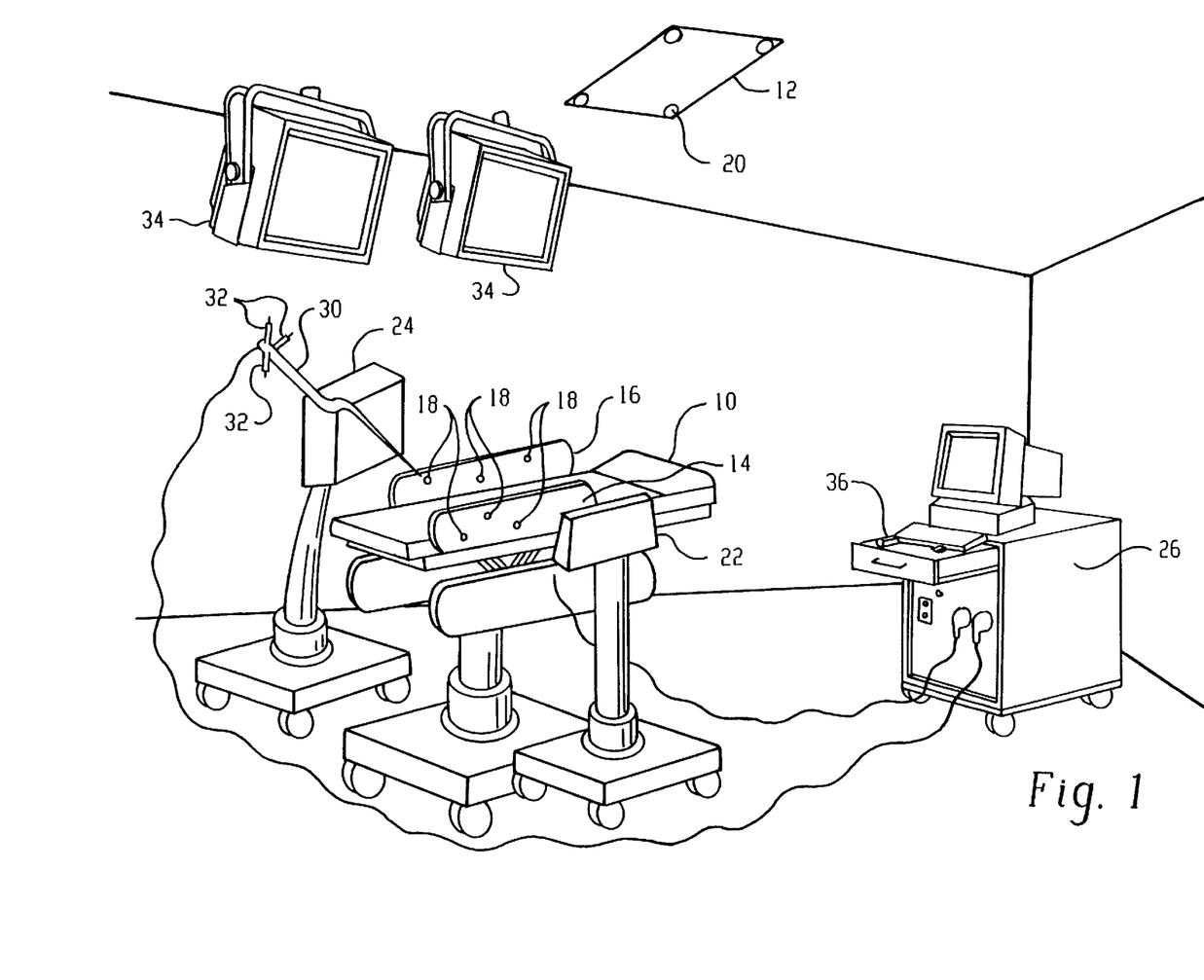
FIG. 1 is a perspective view of an operating room in which the present invention is deployed.

With reference to FIG. 1, a subject, such as a human patient, is supported on an operating table 10 or other subject support. The subject support is positioned stationarily within a procedure room and a region of interest of the subject is held against motion. A frame 12 is mounted in a fixed relationship to the room or the patient support, hence in a fixed relationship to the region of interest of the subject. First and second reference plates 14, 16, respectively, are mounted in a fixed relationship to the region of interest of the subject, in the preferred embodiment fixedly mounted to the subject support. Each reference plate includes a radiotranslucent portion on which a plurality of non-collinear radiopaque markers 18 are affixed or embedded. Preferably, the reference plates are mounted on opposite sides of the region of interest. Alternately, the frame 12, the reference plates 14, 16 and the patient support 10 can be mounted in a fixed relationship to each other such that the patient support and the supported patient can be moved within the procedure room without disrupting the fixed physical relationship between the frame and the region of interest.

The frame supports a plurality of receivers 20 such as video cameras, light sensitive diodes, other light sensitive receivers, radio frequency receivers, acoustic receivers such as microphones, and the like. An x-ray source 22 and a two dimensional x-ray receiver 24 are selectively positionable on opposite sides of the reference plates 14, 16 and the region of interest such that a beam of radiation from the x-ray source passes through the radiopaque markers 18 and the region of interest before striking the x-ray detector 24. For mathematical simplicity, the x-ray source and detector are preferably physically connected together such that they have a known spacing and relationship, such as on a C-arm. The C-arm is preferably mounted for rotation about a known axis of rotation.

Two or more images are taken of the plates and the region of interest at different angular orientations. As is discussed below in conjunction with FIG. 2, these images are analyzed by a computer system 26 to correlate the coordinate system of the region of interest with the coordinate system of the reference plates 14, 16. Typically, the mathematical transform operates on the coordinates of one coordinate in one system to give the coordinates in the other system.

The operator or interventionalist positions the point of a pointer or wand 30 on each of the markers 18. The pointer or wand carries a plurality of emitters 32 which emit signals of an appropriate type to be received by the receivers 20. From the predetermined geometry of the pointer and its emitters and the geometry of the receivers, the location of the tip of the pointer in a coordinate system of the pointer, the receivers, and the interventionalist or the operator is readily determined using conventional algorithms. Once the location of each of the radiopaque reference markers 18 is determined with the pointer in the operator coordinate system, the computer 26 calculates the correlation between operator coordinate system with the reference marker coordinate system, which was previously correlated to the region of interest coordinate system.

Images from the previously generated diagnostic image data are displayed on one of monitors 34 and images from the image data generated by the x-ray detector 24 is displayed on the other monitor. An operator control 36 is utilized by the operator to place cursors or other markers on corresponding anatomical structures on both monitors. In this manner, the diagnostic image coordinate system is correlated with the patient coordinate system. With this series of correlations or transforms, the operator, image data and patient coordinated systems are correlated. The operator can then plan and carry out minimally invasive or other surgical procedures on the patient relying upon the previously generated diagnostic image data and positions and trajectories in the operator coordinate system as designated by the pointer 30 or other tools or appliances which carry emitters.

Figure 2:
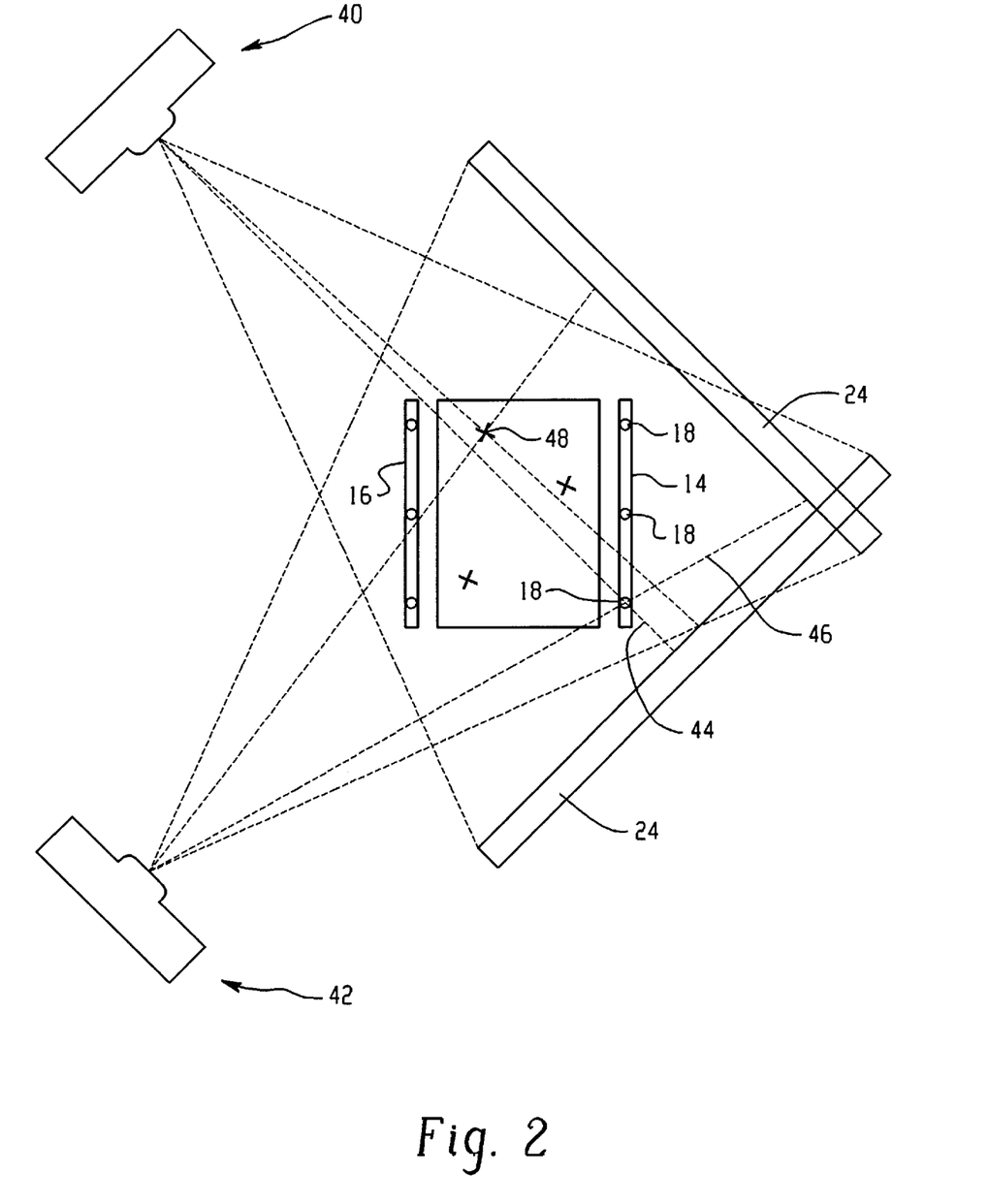
FIG. 2 is a diagrammatic illustration which illustrates correlating reference markers and anatomical markers using projection images.

With reference to FIG. 2, the radiation source 22 is positioned in a first position 40 and projects x-rays through the region of interest onto the radiation detector 24. This generates a first projection image of the radiopaque markers 18. The x-ray tube and detectors are then rotated to a second position 42 and a second projection image is made. It will be noted that when a ray 44 is back projected from the image of one of the radiation opaque markers to the x-ray source in one position and another ray 46 is back projected from the image through the same marker to the radiation source at the other position, the two rays will cross at the radiation opaque marker. Because the position of the radiation opaque markers relative to each other is known, it is a matter of simple geometry to correlate the coordinate system of the markers 18 with the coordinate system of the projection images. Using the analogous geometric principles, the location of any characteristic feature in the region of interest which appears in both projection images can be determined within the coordinate system of the projection images. Because the patient and marker coordinate systems are correlated to a common coordinate system, they are correlated with each other.

Figure 3:
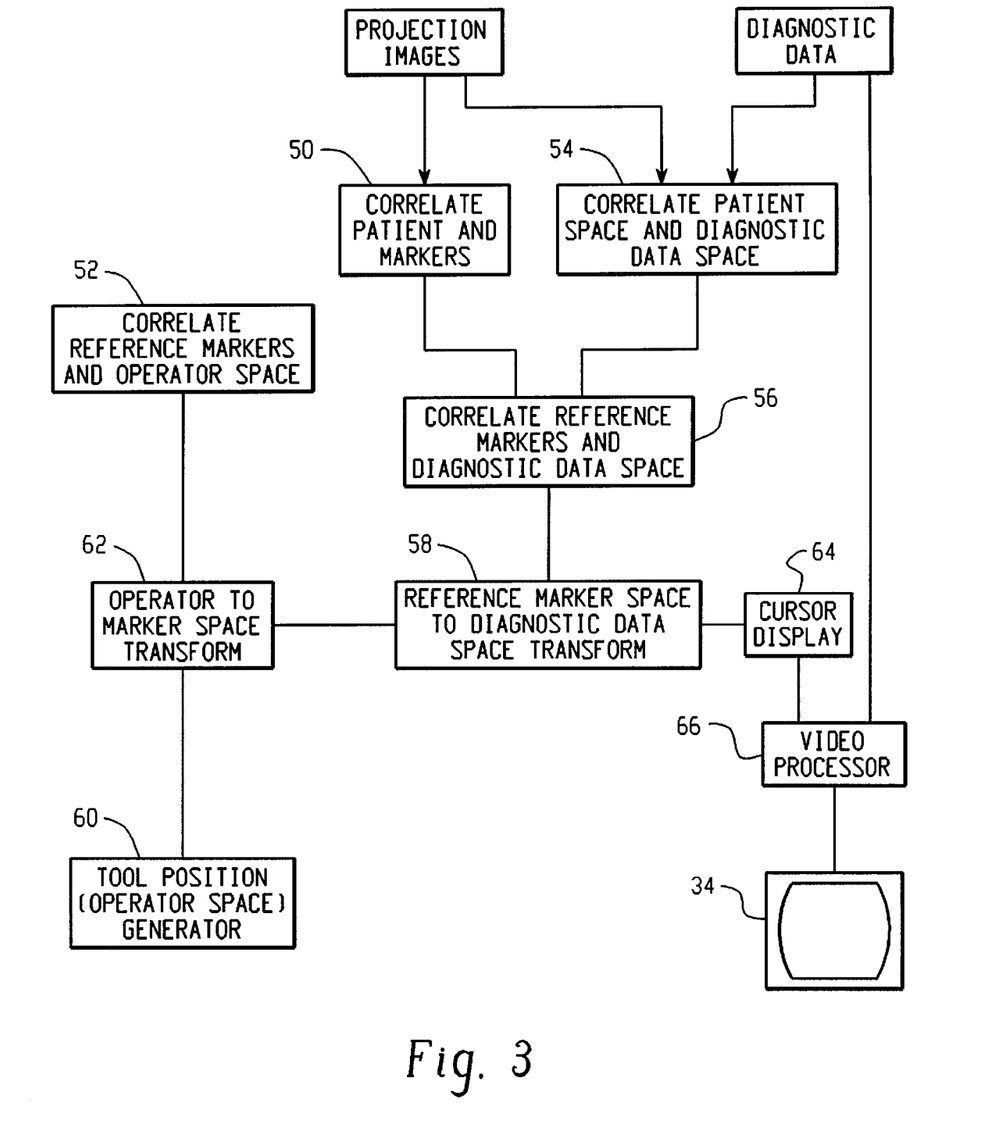
FIG. 3 is a diagrammatic illustration of a system or method for correlating a position of a pointer or tool in operator space with diagnostic image data in diagnostic image space.

With reference to FIG. 3, the coordinates of patient space are correlated with the coordinates of reference marker space by a step or processor 50 by correlating both patient space and marker space with projection image space as discussed above in conjunction with FIG. 2. A step or processor 52 correlates reference marker space with operator space. More particularly, the pointer 30 is touched to each of the reference markers 18 and actuated to determine the position of each of the reference markers in the coordinates of operator space. From the marker space coordinates of the markers and the operator space coordinates of the markers, the step or means 52 determines the relationship or transform between the two spaces.

Once the operator designates corresponding points in the projection images and the diagnostic images, a step or processor 54 correlates patient space with image space. Again, the correlation preferably takes the form of a transform which designates the relationship between the coordinates of patient and image space. A step or means 56 receives the transform or other correlation between patient space and reference marker space from step or processor 50 and the correlation or transform between patient space and image space from the step or processor 54 and calculates a correlation between reference marker space and image space. When the step or processors 50 and 54 generate mathematical transforms, the transforms operate on each other, i.e. are simply combined. To generate a transform which describes the relationship between reference marker space and image space, a processor or step 58 is programmed to implement the marker space into image space transform.

When performing a minimally invasive surgery or other technique, a wand or tool is positioned at proposed locations on the patient and actuated. A processor or step 60 generates the coordinate position and trajectory in operator space of a wand or tool to be applied to the patient is then determined. A processor or step 62 applies the transform between operator space and marker space which is determined by step or process 52. The reference marker coordinates of the wand are transformed by the marker to image space transform step or processor 58 to generate image space coordinates indicative of the point of a pointer and/or a trajectory. An image space cursor/trajectory processor or step 64 generates a cursor display indicative of the point of a pointer or a trajectory of the tool. A video processor or step 66 superimposes the image space cursor and the diagnostic image representation to generate a human readable display for display on one of the monitors 34.

Figure 4:
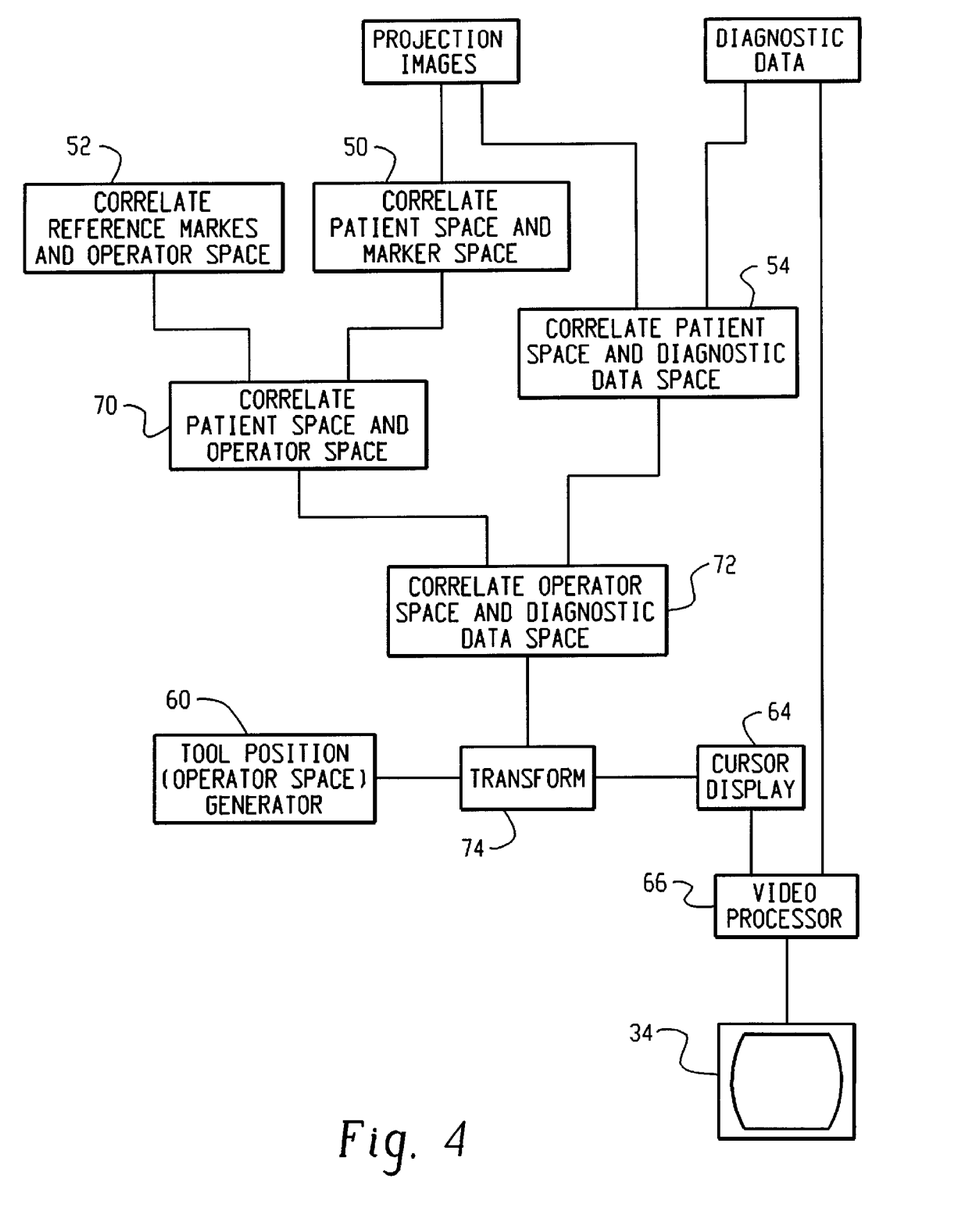
FIG. 4 illustrates an alternate system or method for correlating a pointer or tool position in operator space with diagnostic image data.

It is to be appreciated that the transforms between coordinate systems are linear operators that can be applied in any order. With reference to FIG. 4, the correlation between patient space and reference marker space is again determined by the step or processor 50. The correlation between reference marker space and operator or wand space is determined by the step or processor 52. A step or processor 70 determines the correlation between patient space and operator space. The step or processor 54 correlates patient space with image data space. A step or processor 72 receives the correlation between patient and operator space and the correlation between patient and image space to generate a correlation or transform between operator space and image space. The operator space to image space transform is conveyed to a processor 74 which receives operator space coordinates of a pointer or tool guide or other apparatus and transforms those coordinates into image space such that a cursor can be superimposed on the diagnostic display as discussed above in conjunction with FIG. 3.

The coordinates can be correlated in still other orders. For example, the three dimensional diagnostic image data can be reprojected along rays analogous to those described in FIG. 2 to create reprojected images analogous to the two or more projection images made by the x-ray source 22 and detector 24 described above. The reprojected images are compared with the projection images using any of the various known image comparison algorithms. The direction of reprojection is iteratively adjusted until a best match is achieved. By mapping the images of the markers 18 from the projection images onto the best fit reprojection images and projecting the markers from the reprojected images into data space, the coordinates of the markers in data space are achieved. Once the coordinates of the markers in image space are known, the transform between reference marker space and image space is readily calculated. Again, reference marker space is easily correlated to operator space.

As another example, the two or more projection images from detector 24 are reconstructed into a volume image representation using any of the various reconstruction techniques well known in CT data reconstruction and radio astronomy, for example, filtered back projection. The small number of input images will cause the resultant volume image to have a limited dynamic range rendering it unsuitable for diagnostic imaging. However, sharply defined structures, such as the radiopaque markers and optimal anatomical markers from at least some organs and tissues can be clearly identified in the reconstructed volume image. By comparing the anatomical markers in the reconstructed images and the diagnostic data, the transforms between diagnostic data space and image space and reference marker space are readily determined.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A registration apparatus for bringing (i) a tip of a wand, (ii) anatomy of a subject in a patient space, and (iii) three-dimensional diagnostic image data into registration independently of diagnostic imaging hardware, which wand includes at least three emitters for emitting signals indicative of the position of the wand, at least two receivers for receiving the signals, a first image memory for storing a set of the three-dimensional diagnostic image data indicative of the anatomy of the subject, a selecting means for selecting data from the first image memory, and a display for converting the selected data from the first image memory into human-readable displays, further including:

first and second reference plates positioned at a first location and a second location, respectively, the first and second locations being known and on opposing sides relative to a subject, each reference plate including at least three non-collinear radiopaque marks at known locations;

an x-ray source positionable at each of a third location and a fourth location to project x-rays through the first and second locations;

an x-ray detector positioned at each of a fifth location and a sixth location to receive x-rays projected through the first and second locations from the third and fourth locations, respectively, such that x-rays are projected from the x-ray source, through the reference plates and the subject and onto the x-ray detector to generate a first projection images of the three radiopaque marks and the anatomy when the x-ray detector is positioned at the fifth location when the x-ray source is positioned at the third location and a second projection which when the x-ray detector being positioned at the sixth location and the x-ray source is positioned at the fourth location; and, a correlator for correlating the set of projection images with the three-dimensional diagnostic image data, a position of a tip of a wand relative to the anatomy in the patient space being correlated with the position of the anatomy in the three-dimensional diagnostic image data in accordance with the correlation between the projection images and the diagnostic image data, whereby the wand tip, the anatomy in patient space, and the diagnostic image are correlated independently of x-ray source and the x-ray detector space.

2. A registration apparatus for a diagnostic imaging system, for determining a position of a tip of a wand relative to an anatomy of a subject in a patient space relative to a position of the wand tip and the anatomy in three-dimensional diagnostic image data, which includes at least three emitters for emitting signals indicative of the position of the wand, at least two receivers for receiving the signals, a first image memory for storing the three-dimensional diagnostic image data indicative of the anatomy of the subject, a selecting means for selecting data from the first image memory, and a display for converting the selected data from the first image memory into human-readable displays, further including:

first and second reference plates positioned at a first location and a second location, respectively, the first and second locations being on opposing sides relative to a patient, each reference plate including at least three non-collinear radiopaque marks at known locations;

an x-ray source and an x-ray detector positioned at each of a plurality of locations to project x-rays from the x-ray source, through the reference plates and the patient and onto the x-ray detector to generate projection images of the three radiopaque marks and the anatomy of the patient; and, a correlator for correlating a location of each reference mark in projection image space with the location of the corresponding reference mark in patient space based on offsets, distances, and angles, along with data acquired when the emitters are activated after a tip of a wand is touched to each of the radiopaque marks in the patient space and the radiopaque mark touched by the wand tip is identified in image space, thereby correlating the position of the wand tip relative to the anatomy in the patient space with the position of the anatomy in the three-dimensional diagnostic image data.

3. A method for determining coordinates in an image space, including three-dimensional diagnostic image data of a subject, which correspond to a position of a tip of a wand in a patient space, for use in a system which includes emitters for emitting signals indicative of the position of the wand, receivers for receiving the signals, a subject support, an image memory for storing the diagnostic image data indicative of a three-dimensional region of a portion of the subject which is secured to the subject support means, and a display for converting selected data from the image memory into human-readable displays, the method comprising:

positioning a first reference plate, containing a first set of three non-collinear x-ray opaque reference marks, on a first side of a subject;

positioning a second reference plate, containing a second set of three non-collinear x-ray opaque reference marks, on a second side of the subject such that the subject is disposed between the first and second reference plates;

positioning an x-ray source at a first location relative to the first and second reference plates;

positioning an x-ray detector at a second location relative to the first and second reference plates;

projecting x-rays from the x-ray source, through the reference plates and the subject, to the x-ray detector to generate a first projection image of the anatomy of the subject, the first set of reference marks, and the second set of reference marks;

repositioning the x-ray source and the x-ray detector and projecting x-rays through the subject and the first and second reference points to generate a second projection image; and, correlating the first and second projection images with the diagnostic image data for correlating a diagnostic data space and a projection image space.

4. A method for determining coordinates in three-dimensional diagnostic image data of a subject in image space, which coordinates correspond to positions at which a tip of a wand is positioned in a patient space, a subject support, an image memory for storing the diagnostic image data indicative of a three-dimensional region of a portion of the subject which is secured to the subject support means, and a display for converting selected data from the image memory into human-readable displays, the method comprising:

positioning a first reference plate containing a first set of at least three non-collinear x-ray opaque reference marks, on a first side of the subject;

positioning a second reference plate, containing a second set of at least three non-collinear x-ray opaque reference marks, on a second side of the subject such that the subject is disposed between the first and second reference plates;

positioning an x-ray source and an x-ray detector on opposite sides of the first and second reference plates;

projecting x-rays from the x-ray source, through the reference plates and the subject, to the x-ray detector to generate a first projection image of the anatomy of the subject, the first set of reference marks, and the second set of reference marks;

repositioning the x-ray source and the x-ray detector and projecting x-rays through the subject and the first and second reference points to generate a second projection image;

correlating the first and second projection images with the diagnostic image data;

correlating the reference marks with the diagnostic image data; and, correlating the positions of a wand with the reference marks such that the position of the wand is correlated with the diagnostic image data.

5. The method as set forth in claim 4 further including:

generating a mathematical transform which transforms between reference marker space coordinates and coordinates in the diagnostic image data; and, transforming wand positions using the transform to transform wand positions into diagnostic image coordinates.

6. The method as set forth in claim 5 further including:

generating a human readable display from the diagnostic image data with a cursor at the transformed wand position coordinates superimposed thereon.

7. A method of correlating positions of a tool or tool guide in operator space with coordinates of diagnostic image data in image space, the method comprising:

generating a first projection image through a region of interest of a subject in a first direction;

generating a second projection image through the region of interest in a second projection direction;

identifying corresponding anatomical markers in the first projection image, the second projection image, and the diagnostic image data;

with the corresponding anatomical markers, correlating the first and second projection images with the diagnostic image data to correlate a diagnostic data space and a projection image space;

correlating the projection images with coordinates in operator space to correlate the projection image space with the operator space, within which a tool or a tool guide is positioned adjacent the subject;

during a procedure, determining coordinates of the tool or tool guide in the operator space; and, correlating the position of the tool or tool guide in the operator space with a corresponding position in the diagnostic data space as a function of the correlation between the operator space and the projection image space and the correlation between the projection image space and the diagnostic data space.

8. The method as set forth in claim 7 wherein the step of correlating projection image space with operator space includes:

positioning a plurality of radiopaque markers in a fixed relationship to the region of interest such that the radiopaque markers are imaged in the projection images;

correlating positions of the radiopaque markers in projection image space with coordinates of the anatomical markers in projection image space, such that the correlation between the radiopaque markers and the anatomical markers in projection image space and the correlation between the anatomical markers in projection image space and the anatomical markers in diagnostic data space correlate the position of the radiopaque markers in projection image space with diagnostic data space;

determining coordinates of the radiopaque markers in operator space; and, from the determined positions of the radiopaque markers in operator space and the coordinates of the anatomical markers in projection image space, correlating operator space and projection image space.

9. The method as set forth in claim 7 wherein the step of correlating projection image space with operator space includes:

positioning a plurality of radiopaque markers in a fixed relationship to the region of interest such that the radiopaque markers are imaged in the projection images;

correlating positions of the radiopaque markers in projection image space with coordinates of the anatomical markers in projection image space, such that the correlation between the radiopaque markers and the anatomical markers in projection image space and the correlation between the anatomical markers in projection image space and the anatomical markers in diagnostic data space correlate the position of the radio markers in projection image space with diagnostic data space;

determining coordinates corresponding to the radiopaque markers in diagnostic data space;

determining coordinates of the radiopaque markers in operator space; and, from the determined positions of the radiopaque markers in operator space and the coordinates of the anatomical markers in diagnostic data space, correlating operator space and diagnostic data space.

10. A method of correlating positions of a tool or tool guide in operator space with coordinates of diagnostic image data in image space, the method comprising:

a) generating a first projection image different from the diagnostic image data through a region of interest of a subject in a first direction;

b) generating a second projection image different from the diagnostic image data through the region of interest in a second projection direction;

c) identifying corresponding anatomical markers in the first projection image, the second projection image, and the diagnostic image data;

d) with the corresponding anatomical markers, correlating the projection images with the diagnostic image data to correlate diagnostic data space and projection image space;

e) correlating the projection images with coordinates in operator space to correlate projection image space with operator space, within which a tool or a tool guide is positioned adjacent the subject, the correlating step including:

e1) positioning a Plurality of radiopaque markers in a fixed relationship to the region of interest such that the radiopaque markers are imaged in the projection images;

e2) correlating positions of the radiopaque markers in projection image space with coordinates of the anatomical markers in projection image space, such that the correlation between the radiopaque markers and the anatomical markers in projection image space and the correlation between the anatomical markers in projection image space and the anatomical markers in diagnostic data space correlate the position of the radio markers in projection image space with diagnostic data space;

e3) determining coordinates of the radiopaque markers in operator space, including:

e3a) positioning a tip of a pointer on each of a plurality of the radiopaque markers, each time the tip of the pointer is positioned on one of the radiopaque markers, determining a coordinate of the tip of the pointer in operator space; and, e4) from the determined positions of the radiopaque markers in operator space and the coordinates of the anatomical markers in projection image space, correlating operator space and projection image space;

f) during a procedure, determining coordinates of the tool or tool guide in operator space; and, g) through the correlation between operator space and projection image space and the correlation between projection image space and diagnostic data space, correlating the position of the tool or tool guide in operator space with a corresponding position in diagnostic data space.

11. The method as set forth in claim 10 wherein the step of determining the coordinate of the pointer tip in operator space includes:

actuating a plurality of emitters disposed on the pointer; and, sensing signals emitted by the emitters with at least one receiver mounted in a fixed relation to the subject.

12. The method as set forth in claim 10, wherein the step of correlating positions of the radiopaque markers in projection image space includes:

touching the pointer tip to one of the radiopaque marks in the patient space;

activating the emitters mounted on the pointer;

identifying, in the diagnostic data space, the radiopaque mark touched by the pointer tip; and, correlating a location of each radiopaque marker in the diagnostic data space with the location of the corresponding reference mark in the operator space as a function of data acquired when the emitters are activated.

13. An apparatus for correlating positions of a tool or tool guide in an operator space with coordinates of diagnostic image data in an image space, the apparatus comprising:

a computer memory for storing three dimensional diagnostic image data used for generating diagnostic images;

an x-ray source for projecting x-rays through a region of interest of a subject, the x-ray source being movably mounted to project x-rays through the region of interest from a plurality of directions;

an x-ray detector for detecting x-rays projected through the region of interest and converting received x-rays into electronic projection image data;

a computer processor for generating projection images from the electronic projection data signals received from the x-ray detector;

a radio translucent carrier which carries a plurality of radiopaque reference markers, the radio translucent carrier being selectively positioned adjacent the region of interest between the x-ray source and the x-ray detector, such that the radiopaque reference markers are imaged in the projection images;

a tool or tool guide which carries a plurality of emitters, the tool or tool guide being freely positionable around the region of interest, including the radiopaque reference markers;

a receiver for receiving signals emitted by the emitter;

a coordinate processor for correlating an operator space, shown in the projection images including an image of the tool guide, with an image space, shown in diagnostic images, by generating coordinates of the tool or tool guide in the operator space when the tool guide is actuated and identifying corresponding locations in the image space; and, at least one monitor for selectively displaying the diagnostic images and the projection images.

14. The apparatus as set forth in claim 13 further including:

a cursor control with which the operator places cursors on corresponding anatomical structures in the projection images and images from the diagnostic data; and, a processor for correlating coordinates of the designated anatomical markers in the projection images with coordinates of the designated anatomical markers in the diagnostic image data images to derive a correlation between projection image space and diagnostic data space.

15. The apparatus as set forth in claim 14 further including:

a processor for determining coordinates of the radiopaque markers which appear in the projection images with corresponding coordinates in the diagnostic data space.

16. The apparatus as set forth in claim 14 further including:

a processor for determining coordinates of the radiopaque markers in operator space in response to an operator placing a tip of the tool or tool guide on each of a plurality of radiopaque markers and actuating the emitters; and, a processor for processing correlations between the coordinates of the radiopaque reference markers in operator space, correlations between positions of the radiopaque markers in projection image space, positions of anatomical markers in projection image space and diagnostic data space to determine a transform between the operator space and diagnostic image space.

* * * * *